(12) United States Patent
Reiley et al.

(10) Patent No.: US 6,863,672 B2
(45) Date of Patent: Mar. 8, 2005

(54) STRUCTURES AND METHODS FOR CREATING CAVITIES IN INTERIOR BODY REGIONS

(75) Inventors: Mark A Reiley, Piedmont, CA (US); Arie Scholten, Fremont, CA (US)

(73) Assignee: Kyphon Inc., Sunnyvale, CA (US)

( * ) Notice: Subject to any disclaimer, the term of this patent is extended or adjusted under 35 U.S.C. 154(b) by 0 days.

(21) Appl. No.: 10/208,391

(22) Filed: Jul. 30, 2002

(65) Prior Publication Data

US 2002/0188299 A1 Dec. 12, 2002

Related U.S. Application Data

(62) Division of application No. 09/055,805, filed on Apr. 6, 1998, now Pat. No. 6,440,138.

(51) Int. Cl.[7] .............................................. A61B 17/32
(52) U.S. Cl. ........................................................ 606/79
(58) Field of Search ............................. 606/79, 80, 81, 606/84, 85, 45, 46, 82, 83

(56) References Cited

U.S. PATENT DOCUMENTS

| | | | |
|---|---|---|---|
| 3,181,533 A | | 5/1965 | Heath |
| 3,640,280 A | * | 2/1972 | Slanker et al. ................ 606/84 |
| 3,828,790 A | | 8/1974 | Curtiss et al. |
| 4,203,444 A | * | 5/1980 | Bonnell et al. ............... 604/22 |
| 4,573,448 A | * | 3/1986 | Kambin ...................... 606/170 |
| 4,601,290 A | * | 7/1986 | Effron et al. ............... 606/170 |
| 4,644,951 A | * | 2/1987 | Bays ........................... 606/170 |
| 4,969,888 A | | 11/1990 | Scholten et al. |
| 5,015,255 A | | 5/1991 | Kuslich |
| 5,062,845 A | | 11/1991 | Kuslich et al. |
| 5,100,423 A | | 3/1992 | Fearnot |
| 5,108,404 A | | 4/1992 | Scholten et al. |
| 5,242,461 A | * | 9/1993 | Kortenbach et al. ........ 606/159 |
| 5,269,785 A | * | 12/1993 | Bonutti ....................... 606/80 |
| 5,397,320 A | | 3/1995 | Essig et al. |
| 5,437,665 A | | 8/1995 | Murno |
| 5,439,464 A | * | 8/1995 | Shapiro ....................... 606/83 |
| 5,445,639 A | | 8/1995 | Kuslich et al. |
| 5,496,330 A | | 3/1996 | Bates et al. |
| 5,499,981 A | | 3/1996 | Kordis |
| 5,509,919 A | * | 4/1996 | Young ......................... 606/80 |
| 5,536,267 A | | 7/1996 | Edwards et al. |
| 5,540,693 A | | 7/1996 | Fisher |
| 5,571,098 A | | 11/1996 | Domankevitz |
| 5,582,618 A | * | 12/1996 | Chin et al. .................. 606/170 |
| 5,658,280 A | | 8/1997 | Issa |
| 5,730,704 A | | 3/1998 | Avitall |
| 5,814,044 A | | 9/1998 | Hooven |
| 5,827,312 A | * | 10/1998 | Brown et al. ............... 606/167 |
| 5,876,399 A | | 3/1999 | Chia et al. |
| 5,879,353 A | * | 3/1999 | Terry .......................... 606/85 |
| 5,891,147 A | | 4/1999 | Moskovitz et al. |
| 5,925,039 A | | 7/1999 | Landingham |
| 5,928,239 A | * | 7/1999 | Mirza .......................... 606/79 |
| 5,957,884 A | | 9/1999 | Hooven |
| 5,984,932 A | | 11/1999 | Yoon et al. |
| 6,015,406 A | | 1/2000 | Goble et al. |
| 6,440,138 B1 | | 8/2002 | Reiley et al. |

FOREIGN PATENT DOCUMENTS

DE      G 8800197.0      6/1988

\* cited by examiner

*Primary Examiner*—Eduardo C. Robert
*Assistant Examiner*—David Comstock
(74) *Attorney, Agent, or Firm*—Ryan, Kromholz & Manion

(57) ABSTRACT

Tools carry structures that are deployed inside bone and, when manipulated, cut cancellous bone to form a cavity.

26 Claims, 12 Drawing Sheets

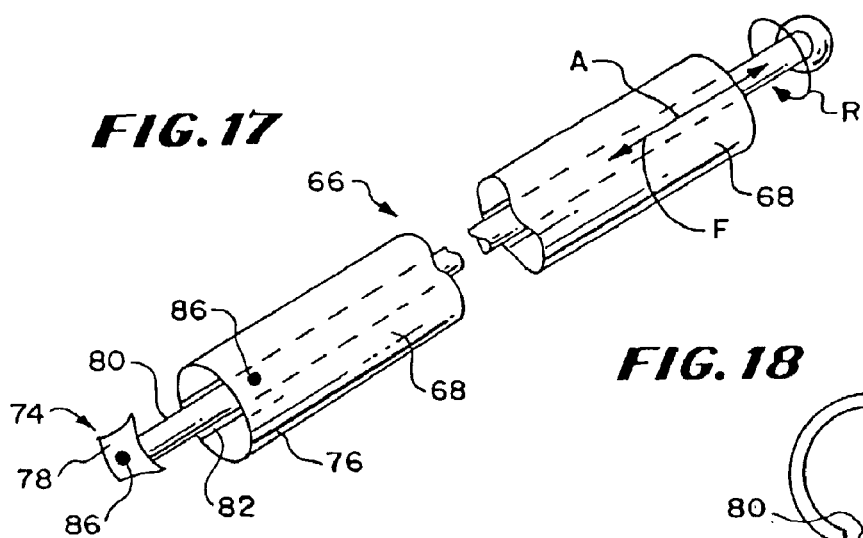
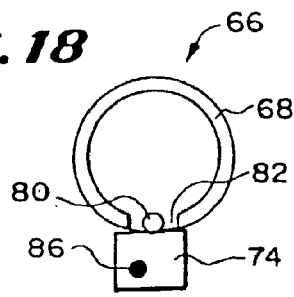
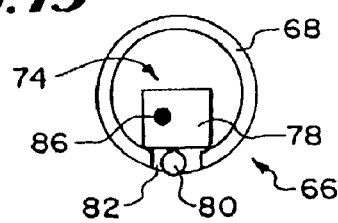
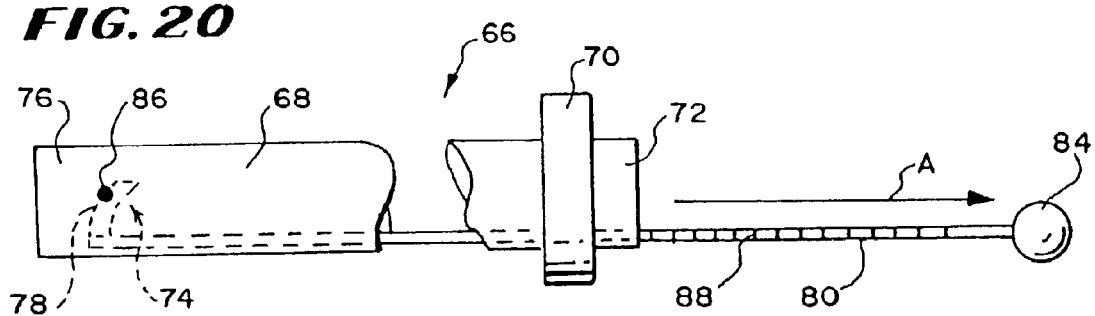
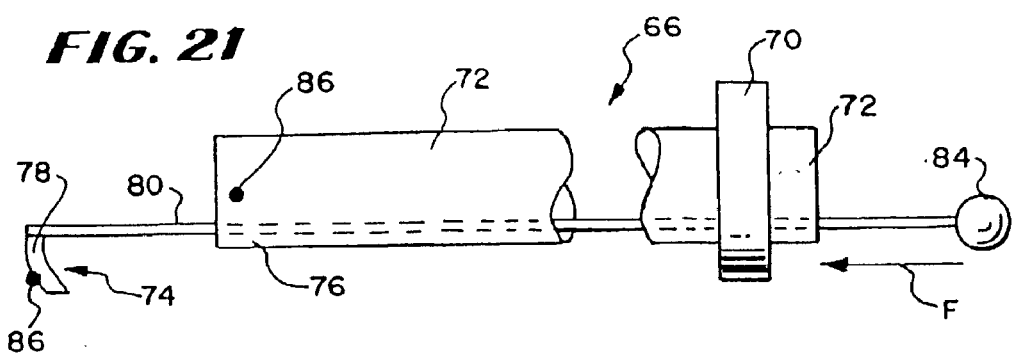

STRUCTURES AND METHODS FOR CREATING CAVITIES IN INTERIOR BODY REGIONS

RELATED APPLICATIONS

This application is a divisional of application Ser. No. 09/055,805, filed Apr. 6, 1998, now U.S. Pat. No. 6,440,138 and entitled "Structures and Methods for Creating Cavities in Interior Body Regions."

FIELD OF THE INVENTION

The invention relates to structures and procedures, which, in use, form cavities in interior body regions of humans and other animals for diagnostic or therapeutic purposes.

BACKGROUND OF THE INVENTION

Certain diagnostic or therapeutic procedures require the formation of a cavity in an interior body region.

For example, as disclosed in U.S. Pat. Nos. 4,969,888 and 5,108,404, an expandable body is deployed to form a cavity in cancellous bone tissue, as part of a therapeutic procedure that fixes fractures or other abnormal bone conditions, both osteoporotic and non-osteoporotic in origin. The expandable body compresses the cancellous bone to form an interior cavity. The cavity receives a filling material, which provides renewed interior structural support for cortical bone.

This procedure can be used to treat cortical bone, which due to osteoporosis, avascular necrosis, cancer, or trauma, is fractured or is prone to compression fracture or collapse. These conditions, if not successfully treated, can result in deformities, chronic complications, and an overall adverse impact upon the quality of life.

A demand exists for alternative systems or methods which, like the expandable body shown in U.S. Pat. Nos. 4,969,888 and 5,108,404, are capable of forming cavities in bone and other interior body regions in safe and efficacious ways.

SUMMARY OF THE INVENTION

The invention provides systems and methods for treating bone. This system comprises a cannula having an axis establishing a percutaneous path leading to inside bone. A shaft is adapted to be deployed inside bone by movement within and along the axis of the cannula. A cavity forming structure is carried by the shaft and comprises a surface which directly contacts and shears cancellous bone in response to linear movement of the shaft along the axis of the cannula.

According to one aspect of the invention, the shaft is flexible.

According to another aspect of the invention, the surface carries at least one marker to aid visualizing the cavity forming structure inside bone. In a preferred embodiment, the marker is made from a radiopaque material.

According to another aspect of the invention, the cavity forming structure comprises a resilient material, e.g., a resilient metal or resilient plastic material.

In yet another aspect of the invention, the cavity forming structure comprises a shape memory material.

According to another aspect of the invention, an element is provided to adjust extension of the cavity forming structure beyond the shaft.

The invention also provides directions for using the system according to a method comprising the steps of providing a cannula having an axis that establishes a percutaneous path leading to bone, providing a shaft adapted to be deployed inside bone including a cavity forming structure carried by the shaft comprising a surface which directly contacts and shears cancellous bone in response to linear movement of the shaft along the axis of the cannula, deploying the cannula percutaneously to establish a path leading to inside bone, introducing the shaft by movement within and along the axis of the cannula to deploy the cavity forming structure inside bone, and moving the shaft linearly along the axis of the cannula to cause the surface to shear cancellous bone and form a cavity. The method for use can also instruct filling the cavity with a material, such as, e.g., bone cement, allograft material, synthetic bone substitute, a medication, or a flowable material that sets to a hardened condition.

Features and advantages of the inventions are set forth in the following Description and Drawings, as well as in the appended claims.

BRIEF DESCRIPTION OF THE DRAWINGS

FIG. 17 is a perspective side view of a tool having a linear movement blade structure capable of forming a cavity in tissue, with the blade structure deployed beyond the associated catheter tube in an operative position for use;

FIG. 18 is an end view of the tool shown in FIG. 17, with the blade structure shown in its operative position for use;

FIG. 19 is an end view of the tool shown in FIG. 17, with the blade structure shown in its rest position within the catheter tube;

FIG. 20 is a side view of the tool shown in FIG. 17, with the blade structure shown in its rest position within the catheter tube, as also shown in an end view in FIG. 18;

FIG. 21 is a side view of the tool shown in FIG. 17, with the blade structure deployed beyond the associated catheter tube in an operative position for use, as also shown in an end view in FIG. 18;

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

The systems and methods embodying the invention can be adapted for use virtually in any interior body region, where the formation of a cavity within tissue is required for a therapeutic or diagnostic purpose. The preferred embodiments show the invention in association with systems and methods used to treat bones. This is because the systems and methods which embody the invention are well suited for use in this environment. It should be appreciated that the systems and methods which embody features of the invention can be used in other interior body regions, as well.

I. Rotatable Cavity Forming Structures

A. Rotatable Loop Structure

Figure 1:
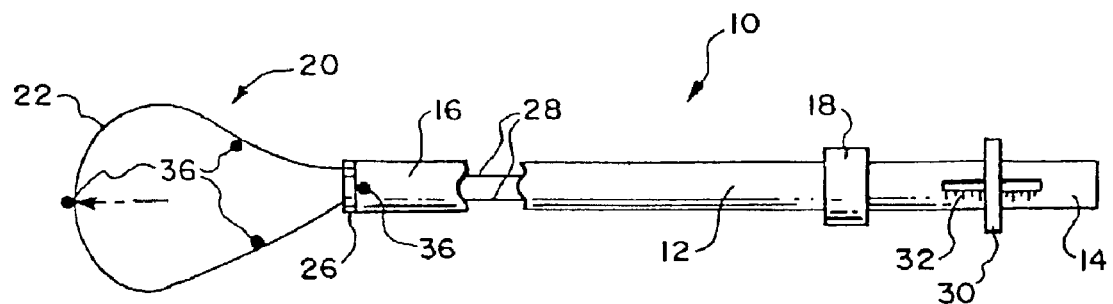
FIG. 1 is a side view of a rotatable tool having a loop structure capable of forming a cavity in tissue, with the loop structure deployed beyond the associated catheter tube.

FIG. 1 shows a rotatable tool 10 capable of forming a cavity in a targeted treatment area. The tool 10 comprises a catheter tube 12 having a proximal and a distal end, respectively 14 and 16. The catheter tube 12 preferable includes a handle 18 to aid in gripping and maneuvering the tube 12. The handle 18 can be made of a foam material secured about the catheter tube 12.

The catheter tube 12 carries a cavity forming structure 20 at its distal end 16. In the illustrated embodiment, the structure 20 comprises a filament 22 of resilient inert material, which is bent back upon itself and preformed with resilient memory to form a loop.

The material from which the filament 22 is made can be resilient, inert wire, like stainless steel. Alternatively, resilient injection molded inert plastic or shape memory material, like nickel titanium (commercially available as Nitinol™ material), can also be used. The filament 22 can, in cross section, be round, rectilinear, or an other configuration.

Figure 1A:
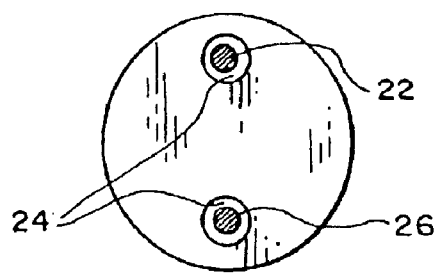
FIG. 1A is an enlarged end view of the tool shown in FIG. 1.

As FIG. 1A shows, the filament 22 radiates from slots 24 in a base 26 carried by the distal end 16 of the catheter tube 12. The free ends 28 of the filament 22 extend through the catheter tube 12 and are connected to a slide controller 30 near the handle 18.

Figure 2:
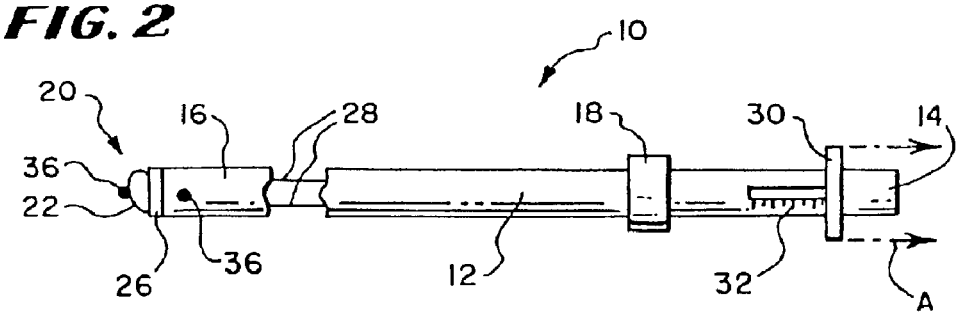
FIG. 2 is a side view of the tool shown in FIG. 1, with the loop structure retracted within the catheter tube.

As FIG. 2 shows, sliding the controller 30 aft (arrow A) retracts the filament 22 through the slots 24, which progressively decreases the dimensions of the loop structure 20. As FIG. 2 shows, in its farthest aft position, the filament 22 is essentially fully withdrawn and does not project a significant distance beyond the distal end 16 of the catheter tube 12.

Figure 3:
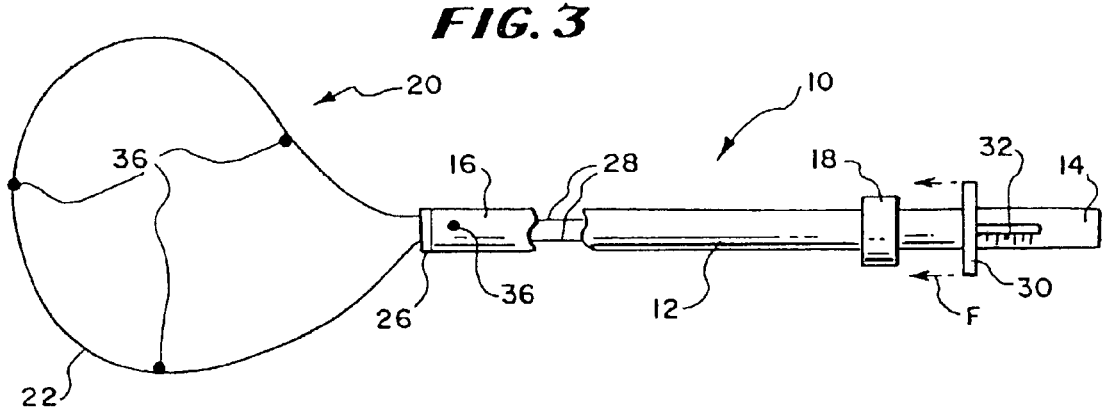
FIG. 3 is a side view of the tool shown in FIG. 1, with the loop structure deployed beyond the catheter tube to a greater extent than shown in FIG. 1.

As FIG. 3 shows, sliding the controller 30 forward (arrow F) advances the filament 22 through the slots 24. The loop structure 20 forms, which projects beyond the distal end 16 of the catheter tube 12. As it is advanced progressively forward through the slots 24, the dimensions of the loop structure 20 progressively increase (compare FIG. 1 to FIG. 3). The controller 30 can include indicia 32, through which the physician can estimate the dimensions of the loop structure 20.

Figure 4:
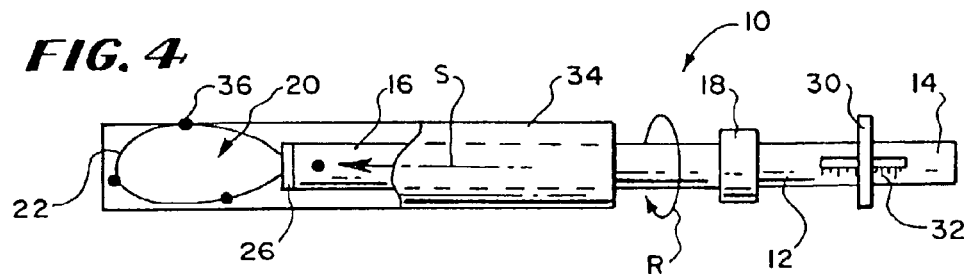
FIG. 4 is a side view of the tool shown in FIG. 1 inserted within a guide sheath for deployment in a targeted treatment area.

In use (see FIG. 4), the catheter tube 12 is carried for axial and rotational movement within a guide sheath or cannula 34. The physician is able to freely slide the catheter tube 12 axially within the guide sheath 34 (arrow S in FIG. 4). As FIG. 4 shows, when fully confined by the guide sheath 34, the loop structure 20, if projecting a significant distance beyond the distal end 16, is collapsed by the surrounding sheath 34. When free of the guide sheath 34, the loop structure 20 springs open to assume its normal dimension. Thereafter, the physician can operate the controller 30 to alter the dimension of the loop structure 20 at will.

When free of the guide sheath 34, the physician is also able to rotate the deployed loop structure 20, by rotating the catheter tube 12 within the guide sheath 34 (arrow R in FIG. 4). As will be described in greater detail alter, rotation of the loop structure 20 slices or cut through surrounding tissue mass.

The materials for the catheter tube 12 are selected to facilitate advancement and rotation of the loop structure 20.

The catheter tube 12 can be constructed, for example, using standard flexible, medical grade plastic materials, like vinyl, nylon, polyethylenes, ionomer, polyurethane, and polyethylene tetraphthalate (PET). The catheter tube 12 can also include more rigid materials to impart greater stiffness and thereby aid in its manipulation and torque transmission capabilities. More rigid materials that can be used for this purpose include stainless steel, nickel-titanium alloys (Nitinol™ material), and other metal alloys.

The filament 22 preferably carries one or more radiological markers 36. The markers 36 are made from known radiopaque materials, like platinum, gold, calcium, tantalum, and other heavy metals. At least one marker 36 is placed at or near the distal extremity of the loop structure 20, while other markers can be placed at spaced apart locations on the loop structure 20. The distal end 16 of the catheter tube 12 can also carry markers. The markers 36 permit radiologic visualization of the loop structure 20 and catheter tube 12 within the targeted treatment area.

Of course, other forms of markers can be used to allow the physician to visualize the location and shape of the loop structure 20 within the targeted treatment area.

B. Rotatable Brush

Figure 5:
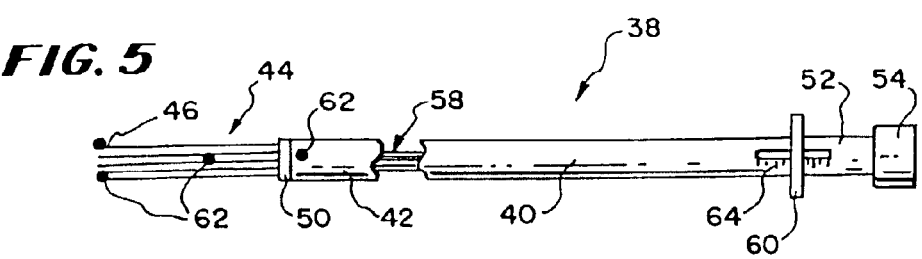
FIG. 5 is a side view of another rotatable tool having a brush structure capable of forming a cavity in tissue, with the brush structure deployed beyond the associated drive tube.

FIG. 5 shows an alternative embodiment of a rotatable tool 38 capable of forming a cavity in a targeted treatment area. The tool 38 comprises a drive shaft 40, which is made from stiffer materials for good torsion transmission capabilities, e.g., stainless steel, nickel-titanium alloys (Nitinol™ material), and other metal alloys.

Figure 5A:
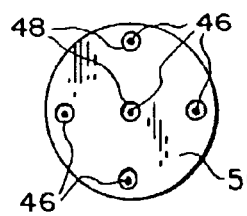
FIG. 5A is an enlarged end view of the tool shown in FIG. 5.

The distal end 42 of the drive shaft carries a cavity forming structure 44, which comprises an array of filaments forming bristles 46. As FIG. 5A shows, the bristles 46 extend from spaced-apart slots 48 in a base 50 carried by the distal end 42 of the drive shaft 40.

The material from which the bristles 46 is made can be stainless steel, or injection molded inert plastic, or shape memory material, like nickel titanium. The bristles 46 can, in cross section, be round, rectilinear, or an other configuration.

Figure 7:
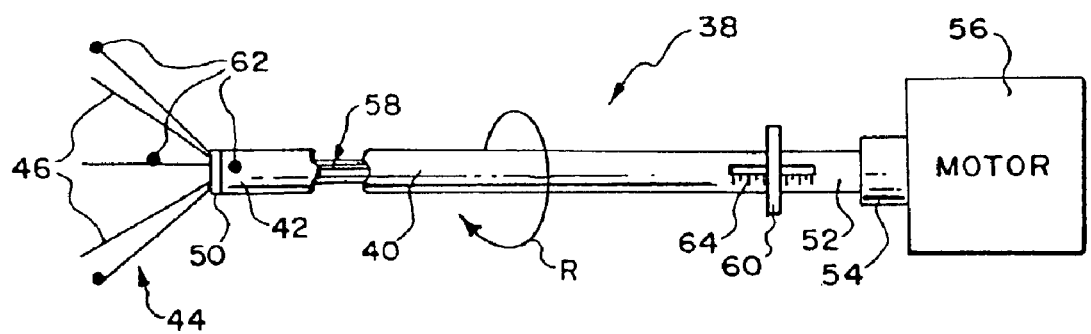
FIG. 7 is a side view of the tool shown in FIG. 5, with the brush structure deployed beyond the catheter tube to a greater extent than shown in FIG. 5, and with the brush structure being rotated to cause the associated bristles to flare outward.
Figure 8:
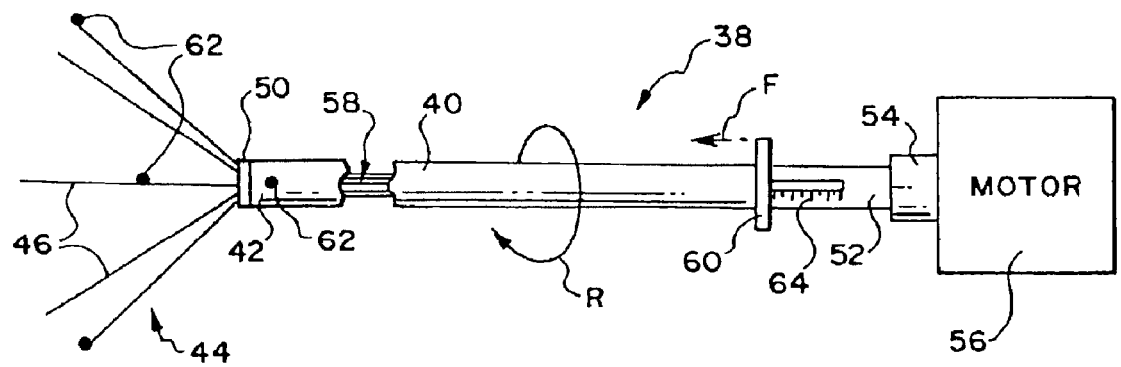
FIG. 8 is a side view of the tool shown in FIG. 7, with the brush structure deployed beyond the catheter tube to a greater extent than shown in FIG. 7, and with the brush structure still being rotated to cause the associated bristles to flare outward.

The proximal end 52 of the drive shaft 40 carries a fitting 54 that, in use, is coupled to an electric motor 56 for rotating the drive shaft 40, and, with it, the bristles 46 (arrows R in FIGS. 7 and 8). When rotated by the motor 46, the bristles spread apart (as FIG. 7 shows), under the influence of centrifugal force, forming a brush-like structure 44. The brush structure 44, when rotating, cuts surrounding tissue mass in the targeted treatment area.

Figure 6:
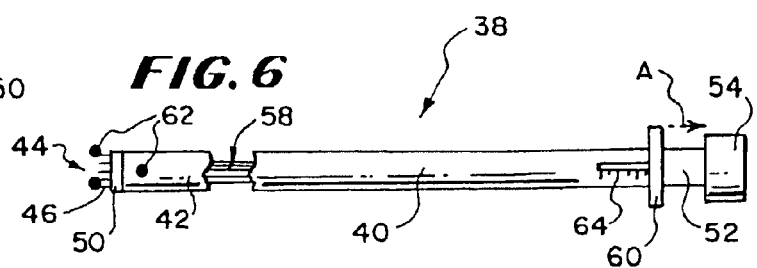
FIG. 6 is a side view of the tool shown in FIG. 5, with the brush structure retracted within the drive tube.

The free ends 58 of the bristles 46 extend through the drive shaft 40 and are commonly connected to a slide controller 60. As FIG. 6 shows, sliding the controller 60 aft (arrow A in FIG. 6) shortens the distance the bristles 46 extend from the base 50. As FIGS. 7 and 8 show, sliding the controller 60 forward (arrow F in FIG. 8) lengthens the extension distance of the bristles 46. Using the controller 60, the physician is able to adjust the dimension of the cutting area (compare FIG. 7 and FIG. 8).

The array of bristles 46 preferably includes one or more radiological markers 62, as previously described. The markers 62 allow radiologic visualization of the brush structure 44 while in use within the targeted treatment area. The controller 60 can also include indicia 64 by which the physician can visually estimate the bristle extension distance. The distal end 42 of the drive shaft 40 can also carry one or more markers 62.

The drive shaft 40 of the tool 38 is, in use, carried for axial and rotational movement within the guide sheath or cannula 34, in the same manner shown for the tool 10 in FIG. 4. The physician is able to freely slide the drive shaft 40 axially within the guide sheath to deploy it in the targeted treatment area. Once connected to the drive motor 56, the drive shaft 40 is free to rotate within the guide sheath 34 to form the brush structure 44.

Figure 9:
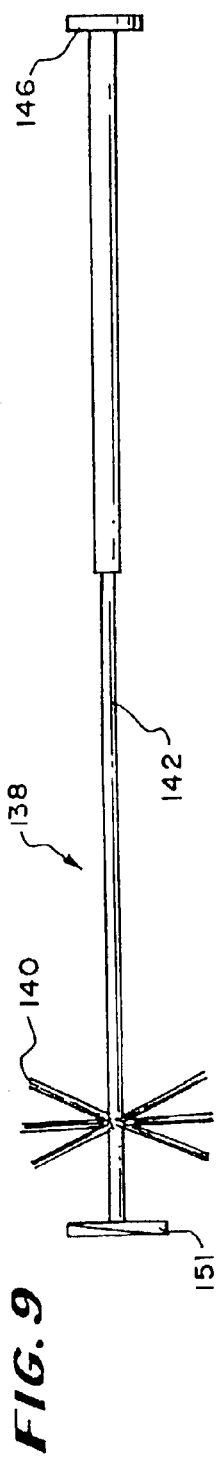
FIG. 9 is a side view of an alternative tool having an array of bristles carried by a flexible shaft, which is capable of forming a cavity in tissue.

FIG. 9 shows an alternative embodiment of a rotatable tool 138 having an array of filaments forming bristles 140, which is capable of forming a cavity in a targeted treatment area. The tool 138 includes a flexible drive shaft 142, which is made, e.g., from twisted wire filaments, such stainless steel, nickel-titanium alloys (Nitinol™ material), and other metal alloys.

The bristles 140 radially extend from the drive shaft 142, near its distal end. The bristles 140 can be made, e.g., from resilient stainless steel, or injection molded inert plastic, or shape memory material, like nickel titanium. The bristles 140 can, in cross section, be round, rectilinear, or an other configuration.

Figure 10:
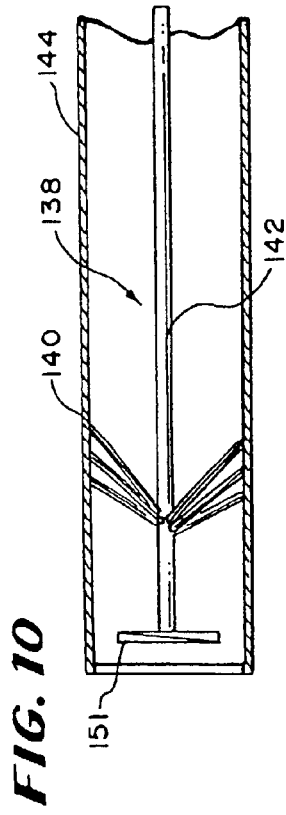
FIG. 10 is a side view of the tool shown in FIG. 9 as it is being deployed inside a cannula.

As FIG. 10 shows, the tool 138 is introduced into the targeted tissue region through a cannula 144. When in the cannula 144, the resilient bristles 140 are compressed rearward to a low profile, enabling passage through the cannula. When free of the cannula 144, the resilient bristles 140 spring radially outward, ready for use.

The proximal end of the drive shaft 142 carries a fitting 146 that, in use, is coupled to an electric motor 148. The motor 148 rotates the drive shaft 142 (arrow R in FIG. 11), and, with it, the bristles 140.

Figure 11:
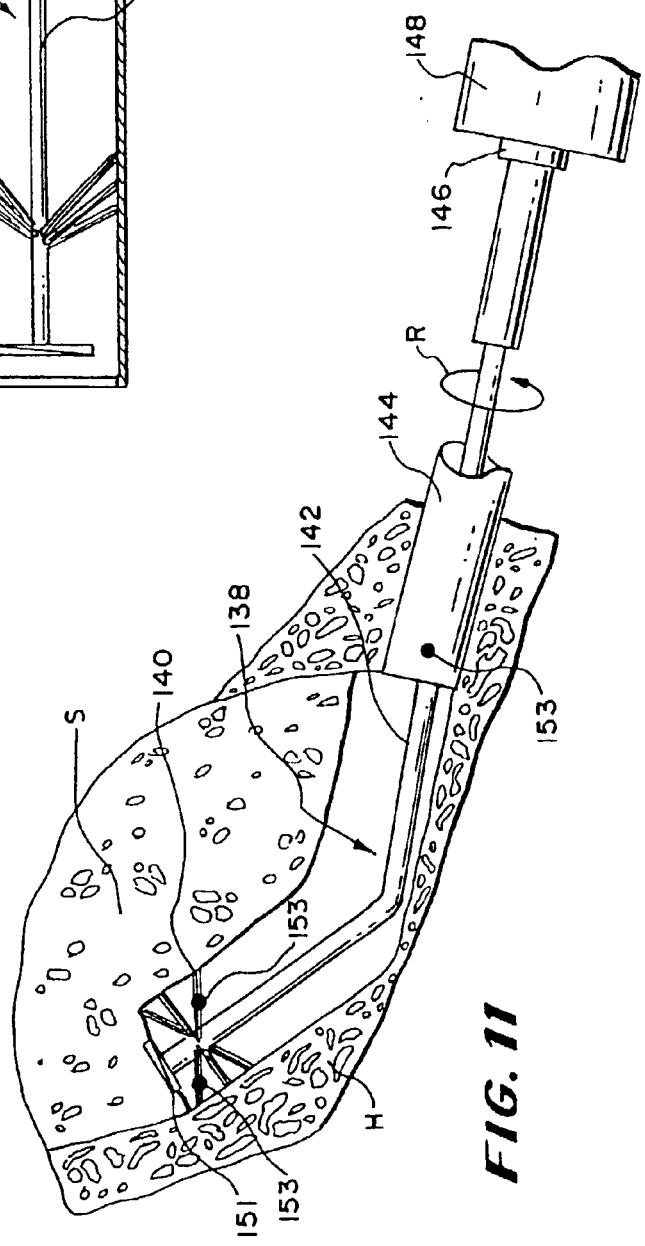
FIG. 11 is the tool shown in FIG. 9 when deployed in a soft tissue region bounded by hard tissue.

As FIG. 11 shows, when deployed inside an interior body cavity with soft tissue S (e.g., cancellous bone bounded by hard tissue H (e.g., cortical bone), the physician can guide the tool 138 through the soft tissue S by allowing the rotating bristles 140 to ride against the adjoining hard tissue H. The flexible drive shaft 142 bends to follow the contour of the hard tissue H, while the rotating bristles 140 cut adjoining soft tissue S, forming a cavity C.

In the illustrated embodiment, the drive shaft 142 carries a pitched blade 151 at its distal end. The blade 151 rotates with the drive shaft 142. By engaging tissue, the blade 151 generates a forward-pulling force, which helps to advance the drive shaft 142 and bristles 140 through the soft tissue mass.

In the illustrated embodiment, the bristles 140, or the cannula 144, or both include one or more radiological markers 153, as previously described. The markers 153 allow radiologic visualization of the bristles 140 while rotating and advancing within the targeted treatment area.

C. Rotatable Blade Structure

Figure 12:
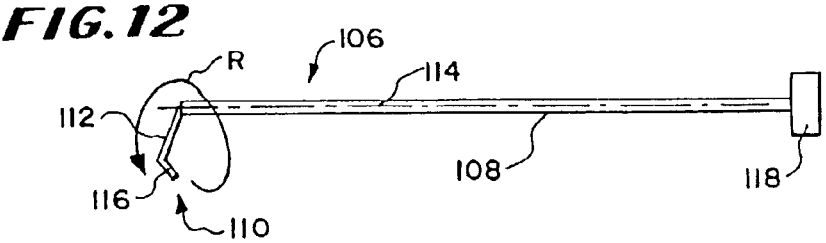
FIG. 12 is a side view of a tool having a rotatable blade structure capable of forming a cavity in tissue.

FIG. 12 shows an alternative embodiment of a rotatable tool 106 capable of forming a cavity in a targeted treatment area. The tool 106, like the tool 38, comprises a generally stiff drive shaft 108, made from, e.g., stainless steel, nickel-titanium alloys (Nitinol™ material), and other metal alloys, for good torsion transmission capabilities.

The distal end of the drive shaft 108 carries a cavity forming structure 110, which comprises a cutting blade. The blade 110 can take various shapes.

Figure 13:
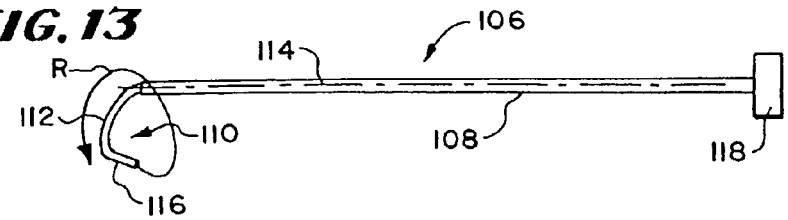
FIG. 13 is a side view of an alternative curved blade structure that the tool shown in FIG. 12 can incorporate.

In FIGS. 12 and 13, the blade 110 is generally L-shaped, having a main leg 112 and a short leg 116. In the illustrated embodiment, the main leg 112 of the blade 110 is pitched radially forward of the drive shaft axis 114, at a small forward angle beyond perpendicular to the drive shaft. The main leg 112 may possess a generally straight configuration (as FIG. 12 shows), or, alternatively, it may present a generally curved surface (as FIG. 13 shows). In the illustrated embodiment, the short leg 116 of the blade 110 is also pitched at a small forward angle from the main leg 112, somewhat greater than perpendicular.

Figure 14:
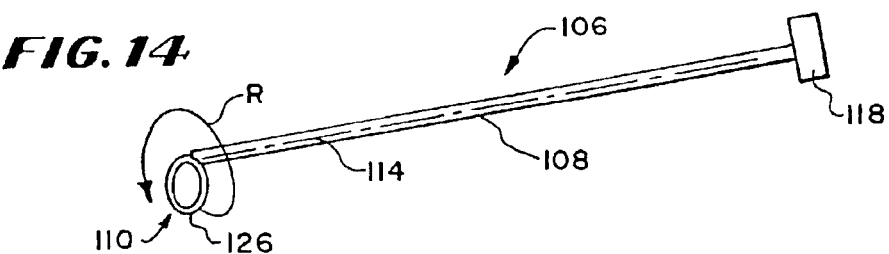
FIG. 14 is a side view of an alternative ring blade structure that the tool shown in FIG. 12 can incorporate.

In FIG. 14, the blade 110 takes the shape of a continuous ring 126. As illustrated, the ring 126 is pitched slightly forward, e.g., at an angle slightly greater than perpendicular relative to the drive shaft axis 114.

The material from which the blade 110 is made can be stainless steel, or injection molded inert plastic. The legs 112 and 116 of the blade 110 shown in FIGS. 12 and 13, and the ring 126 shown in FIG. 14, can, in cross section, be round, rectilinear, or an other configuration.

When rotated (arrow R), the blade 110 cuts a generally cylindrical path through surrounding tissue mass. The forward pitch of the blade 110 reduces torque and provides stability and control as the blade 110 advances, while rotating, through the tissue mass.

Rotation of the blade 110 can be accomplished manually or at higher speed by use of a motor. In the illustrated embodiment, the proximal end of the drive shaft 108 of the tool 106 carries a fitting 118. The fitting 118 is coupled to an electric motor 120 to rotate the drive shaft 108, and, with it, the blade 110.

Figure 15:
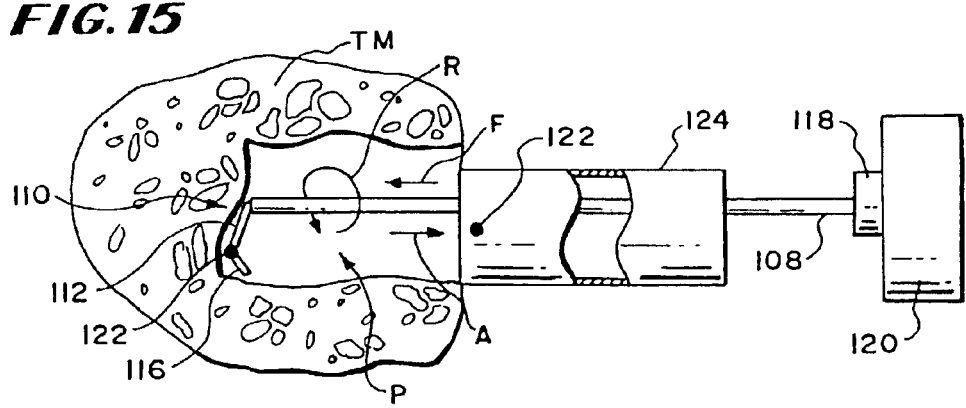
FIG. 15 is a side view of the ring blade structure shown in FIG. 14 while being introduced through a cannula.

As FIG. 15 shows, the drive shaft 108 of the tool 108 is deployed subcutaneously into the targeted tissue area through a guide sheath or cannula 124. Connected to the drive motor 120, the drive shaft 108 rotates within the guide sheath 34, thereby rotating the blade 110 to cut a cylindrical path P in the surrounding tissue mass TM. The blade 110 can be advanced and retracted, while rotating, in a reciprocal path (arrows F and A), by applying pushing and pulling forces upon the drive shaft 108. The blade 110 can also be withdrawn into the cannula 124 to allow changing of the orientation of the cannula 124. In this way, successive cylindrical paths can be cut through the tissue mass, through rotating and reciprocating the blade 110, to thereby create a desired cavity shape.

The blade 110, or the end of the cannula 124, or both can carry one or more radiological markers 122, as previously described. The markers 122 allow radiologic visualization of the blade 110 and its position relative to the cannula 34 while in use within the targeted treatment area.

D. Rinsing and Aspiration

Figure 16:
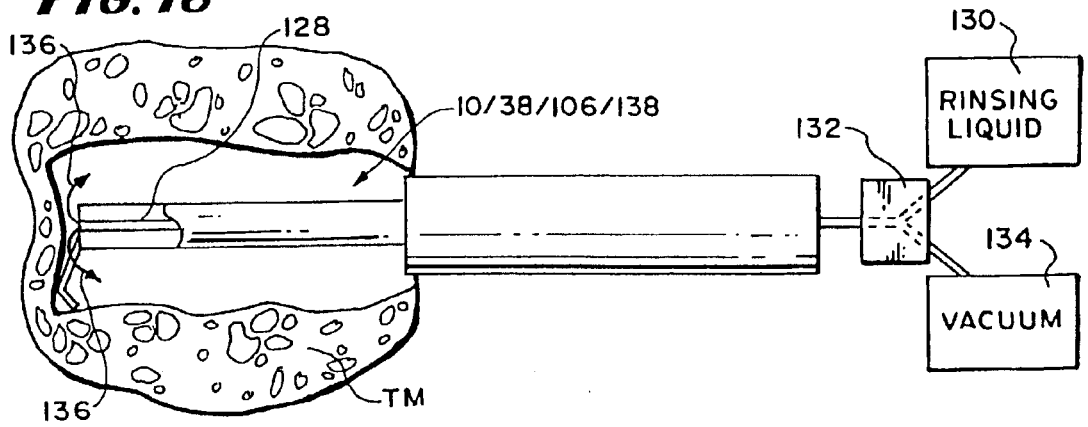
FIG. 16 is a side view of a rotating tool capable of forming a cavity in tissue, with an associated lumen to introduce a rinsing liquid and aspirate debris.

As FIG. 16 shows, any of the tools 10, 38, 106, or 138 can include an interior lumen 128. The lumen 128 is coupled via a Y-valve 132 to a external source 130 of fluid and an external vacuum source 134.

A rinsing liquid 136, e.g., sterile saline, can be introduced from the source 130 through the lumen 128 into the targeted tissue region as the tools 10, 38, or 106 rotate and cut the tissue mass TM. The rinsing liquid 136 reduces friction and conducts heat away from the tissue during the cutting operation. The rinsing liquid 136 can be introduced continuously or intermittently while the tissue mass is being cut. The rinsing liquid 136 can also carry an anticoagulant or other anti-clotting agent.

By periodically coupling the lumen 128 to the vacuum source 134, liquids and debris can be aspirated from the targeted tissue region through the lumen 128.

II. Linear Movement Cavity Forming Structures

A. Cutting Blade

FIGS. 17 to 21 show a linear movement tool 66 capable of forming a cavity in a targeted treatment area. Like the tool 10, the tool 66 comprises a catheter tube 68 having a handle 70 (see FIG. 20) on its proximal end 72 to facilitate gripping and maneuvering the tube 68.

The catheter tube 68 carries a linear movement cavity forming structure 74 at its distal end 76. In the illustrated embodiment, the structure 56 comprises a generally rigid blade 78, which projects at a side angle from the distal end 76 (see FIGS. 17 and 21). The blade 78 can be formed from stainless steel or cast or molded plastic.

A stylet 80 is carried by an interior track 82 within the catheter tube 68 (see FIGS. 18 and 19). The track 82 extends along the axis of the catheter tube 68. The stylet 80 is free to move in a linear aft path (arrow A in FIG. 20) and a linear forward path (arrow F in FIG. 21) within the track 82. The stylet 80 is also free to rotate within the track 82 (arrow R in FIG. 17).

The far end of the stylet 80 is coupled to the blade 78. The near end of the stylet 80 carries a control knob 84. By rotating the control knob 84, the physician rotates the blade 78 between an at rest position, shown in FIGS. 19 and 20, and an operating position, shown in FIGS. 17, 18, and 21. When in the at rest position, the physician can push or pull upon the control knob 84 to move the blade 78 in a linear path within the catheter tube (see FIG. 20). By pushing on the control knob 84, the physician can move the blade 78 outside the catheter tube 68, where it can be rotated into the operating condition (see FIG. 21). When in the operating position, pushing and pulling on the control knob 84 moves the blade in linear strokes against surrounding tissue mass.

In use, the catheter tube 68 is also carried for sliding and rotation within the guide sheath or cannula 34, in the same manner shown in FIG. 4. The physician is able to freely slide the catheter tube 68 axially within the guide sheath 34 to deploy the tool 66 in the targeted treatment site. When deployed at the site, the physician can deploy the blade 78 in the operating condition outside the catheter tube 68 and slide the blade 78 along tissue in a linear path. Linear movement of the blade 78 along tissue cuts the tissue. The physician is also able to rotate both the catheter tube 68 within the guide sheath 34 and the blade 78 within the catheter tube 68 to adjust the orientation and travel path of the blade 78.

The blade 78 can carry one or more radiological markers 86, as previously described, to allow radiologic visualization of the blade 78 within the targeted treatment area. Indicia 88 on the stylet 80 can also allow the physician to visually approximate the extent of linear or rotational movement of the blade 78. The distal end 76 of the catheter tube 68 can also carry one or more markers 86.

B. Energy Transmitters

Figure 22:
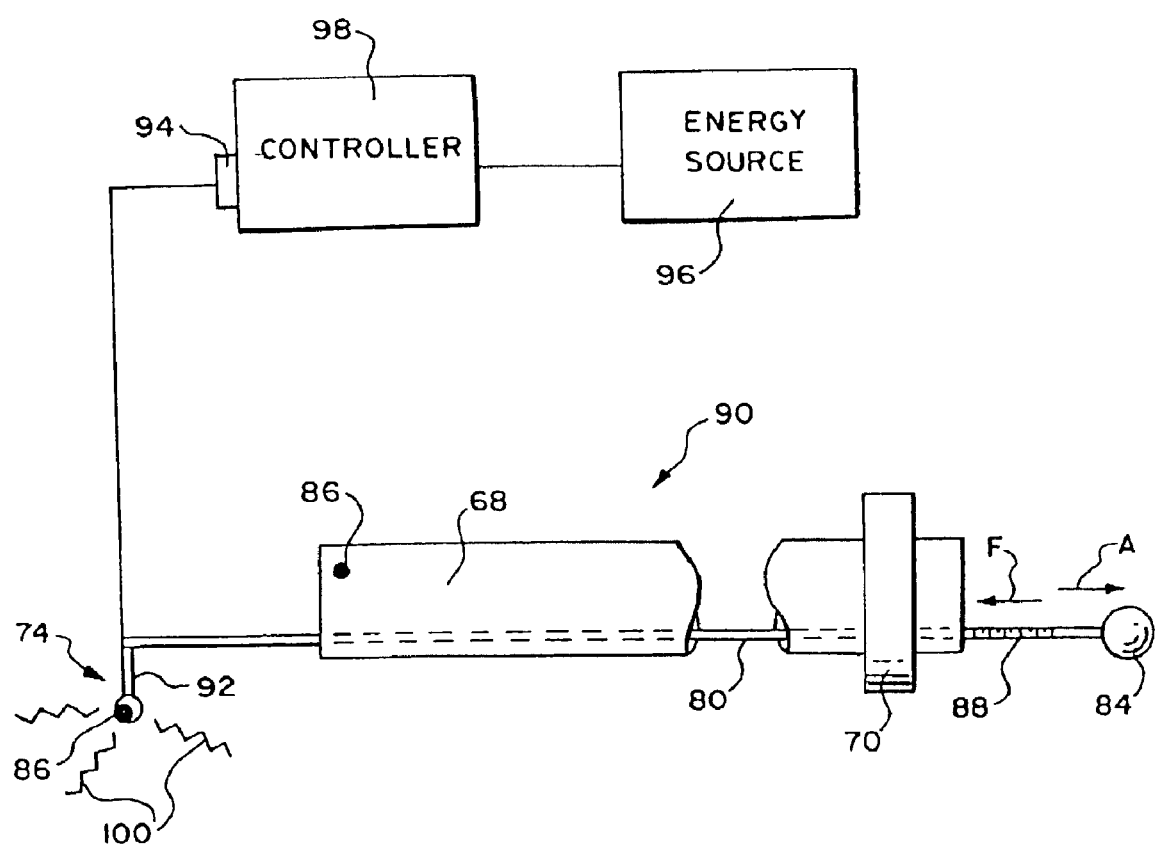
FIG. 22 is a side view of a tool having a linear movement energy transmitter capable of forming a cavity in tissue, with the energy transmitter deployed beyond the associated catheter tube in an operative position for use.

FIG. 22 shows an alternative embodiment of a linear movement tool 90 capable of forming a cavity in a targeted treatment area. The tool 90 is physically constructed in the same way as the linear movement tool 66 just described, so common reference numerals are assigned.

However, for the tool 90 shown FIG. 22, the far end of the stylet 80 carries, not a cutting blade 78, but instead a transmitter 92 capable of transmitting energy that cuts tissue (shown by lines 100 in FIG. 22). A connector 94 couples the transmitter 92 to a source 96 of the energy, through a suitable energy controller 98.

The type of energy 100 that the transmitter 92 propagates to remove tissue in the targeted treatment area can vary. For example, the transmitter 92 can propagate ultrasonic energy at harmonic frequencies suitable for cutting the targeted tissue. Alternatively, the transmitter 92 can propagate laser energy at a suitable tissue cutting frequency.

As before described, the near end of the stylet 80 includes a control knob 84. Using the control knob 84, the physician is able to move the transmitter 92 in a linear path (arrows A and F in FIG. 22) between a retracted position, housed with the catheter tube 68 (like the blade 78 shown in FIG. 20), and a range of extended positions outside the catheter tube 68, as shown in FIG. 22).

As also described before, the catheter tube 68 of the tool 90 is, in use, carried for sliding and rotation within the guide sheath or cannula 34. The physician slides the catheter tube 68 axially within the guide sheath 34 for deployment of the tool 90 at the targeted treatment site. When deployed at the site, the physician operates the control knob 84 to linearly move and rotate the transmitter 92 to achieve a desired position in the targeted treatment area. The physician can also rotate the catheter tube 68 and thereby further adjust the location of the transmitter 92.

The transmitter 92 or stylet 80 can carry one or more radiological markers 86, as previously described, to allow radiologic visualization of the position of the transmitter 92 within the targeted treatment area. Indicia 88 on the stylet 80 can also allow the physician to visually estimate the position of the transmitter 92. The distal end 76 of the catheter tube 68 can also carry one or more markers 86.

III. Use of Cavity Forming Tools

Use of the various tools 10 (FIGS. 1 to 4), 38 (FIGS. 5 to 8), 138 (FIGS. 9 to 11), 106 (FIGS. 12 to 15), 66 (FIGS. 17 to 21), and 90 (FIG. 22) will now be described in the context of deployment in a human vertebra 150.

Figure 23:
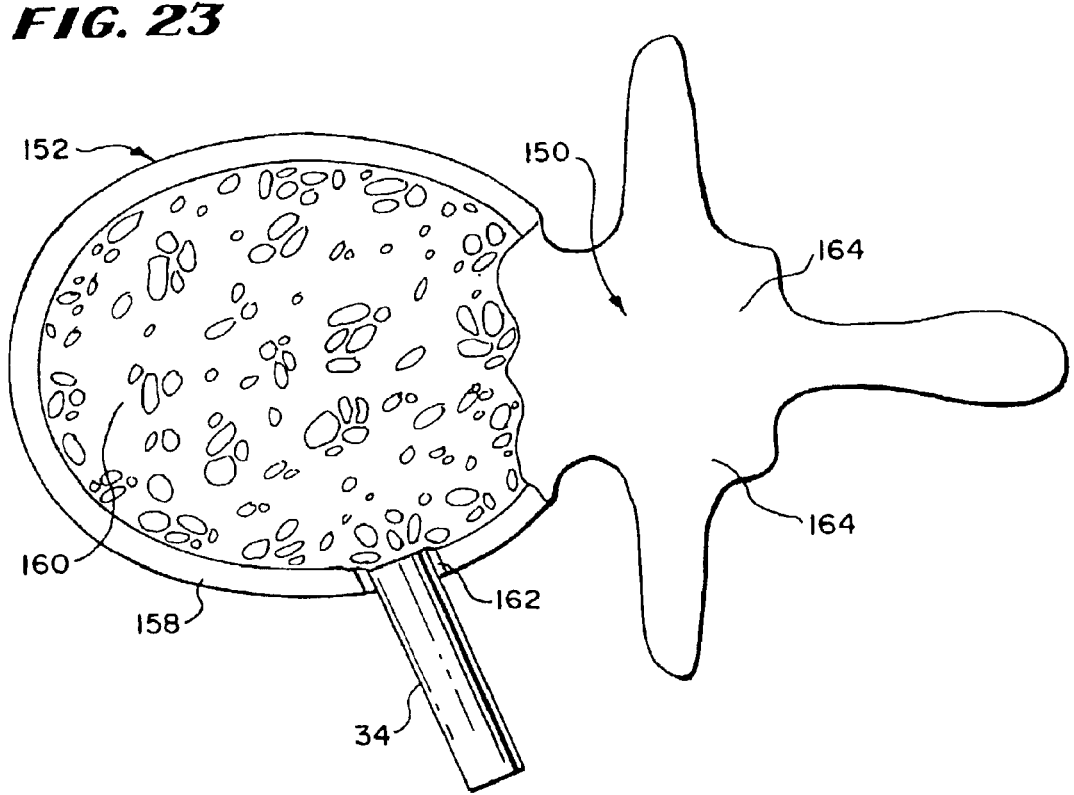
FIG. 23 is a top view of a human vertebra, with portions removed to reveal cancellous bone within the vertebral body, and with a guide sheath located for postero-lateral access.
Figure 24:
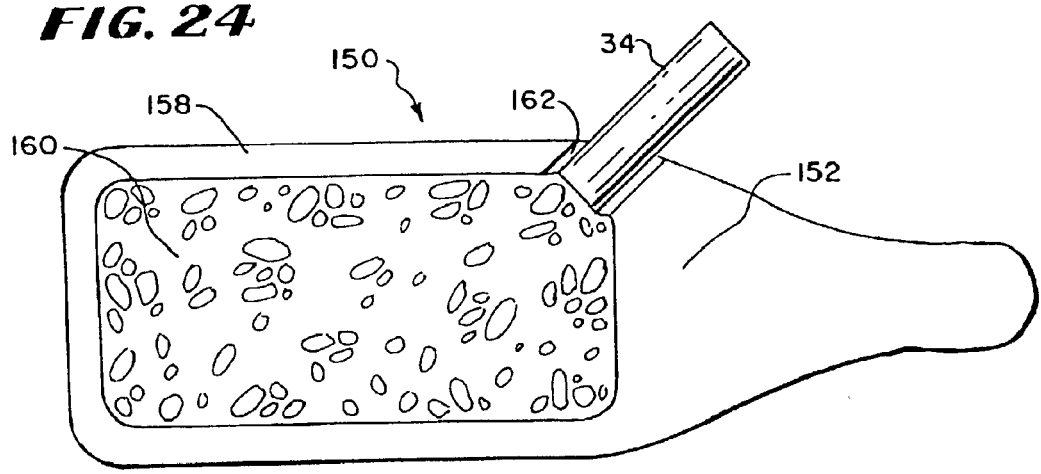
FIG. 24 is a side view of the vertebra shown in FIG. 23.

FIG. 23 shows the vertebra 150 in coronal (top) view, and FIG. 24 shows the vertebra 150 in lateral (side) view. It should be appreciated, however, the tool is not limited in its application to vertebrae. The tools 10, 38, 138, 106, 66, and 90 can be deployed equally as well in long bones and other bone types.

As FIGS. 23 and 24 show, the vertebra 150 includes a vertebral body 152, which extends on the anterior (i.e., front or chest) side of the vertebra 150. The vertebral body 152 includes an exterior formed from compact cortical bone 158. The cortical bone 158 encloses an interior volume of reticulated cancellous, or spongy, bone 160 (also called medullary bone or trabecular bone).

The vertebral body 152 is in the shape of an oval disk. As FIGS. 23 and 24 show, access to the interior volume of the vertebral body 152 can be achieved. e.g., by drilling an access portal 162 through a side of the vertebral body 152, which is called a postero-lateral approach. The portal 162 for the postero-lateral approach enters at a posterior side of the body 152 and extends at angle forwardly toward the anterior of the body 152. The portal 162 can be performed either with a closed, minimally invasive procedure or with an open procedure.

Alternatively, access into the interior volume can be accomplished by drilling an access portal through either pedicle 164 (identified in FIG. 23). This is called a transpedicular approach. It is the physician who ultimately decides which access site is indicated.

As FIGS. 23 and 24 show, the guide sheath 34 (earlier shown in FIG. 4) is located in the access portal 162. Under radiologic or CT monitoring, a selected one of the tools 10, 38, 66, or 90 can be introduced through the guide sheath 34.

A. Deployment and Use of the Loop Tool in a Vertebral Body

When, for example, the loop tool 10 is used, the loop structure 20 is, if extended, collapsed by the guide sheath 34 (as shown in FIG. 4), or otherwise retracted within the catheter tube 12 (as FIG. 2 shows) during passage through the guide sheath 34.

Figure 25:
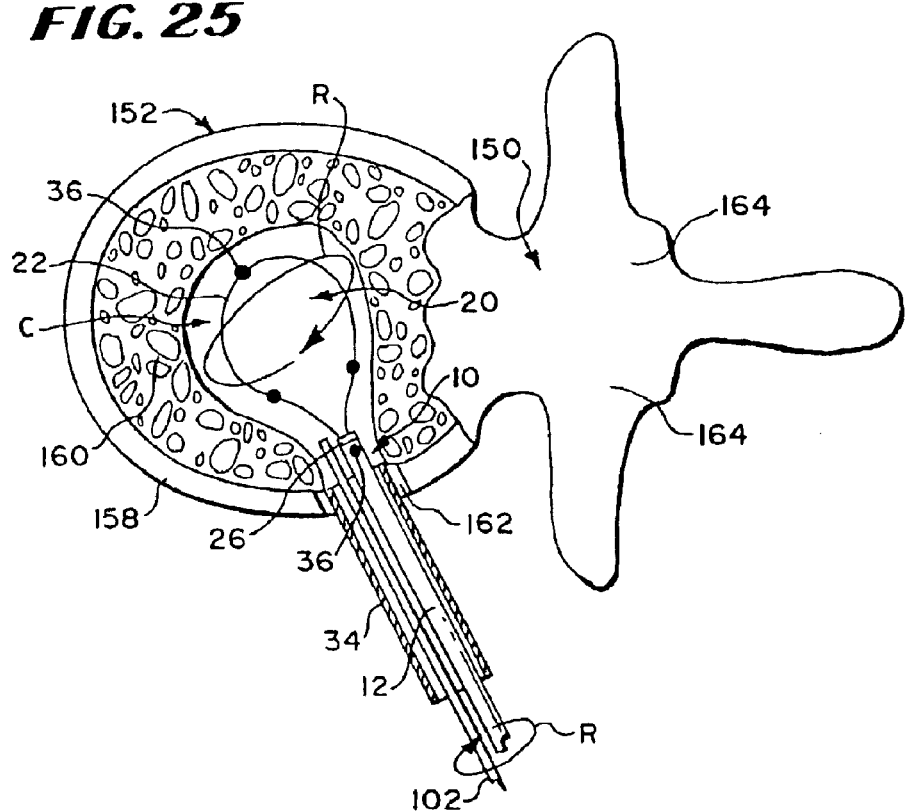
FIG. 25 is a top view of the vertebra shown in FIG. 23, with the tool shown in FIG. 1 deployed to cut cancellous bone by rotating the loop structure, thereby forming a cavity.

Referring to FIG. 25, when the loop tool 10 is deployed outside the guide sheath 34 in the cancellous bone 160, the physician operates the controller 30 in the manner previously described to obtain a desired dimension for the loop structure 20, which can be gauged by radiologic monitoring using the on-board markers 36. The physician manually rotates the loop structure 20 through surrounding cancellous bone 160 (as indicated by arrows R in FIG. 25). The rotating loop structure 20 cuts cancellous bone 160 and thereby forms a cavity C. A suction tube 102, also deployed through the guide sheath 34, removes cancellous bone cut by the loop structure 20. Alternatively, the catheter tube 12 can include an interior lumen 128 (as shown in FIG. 16) to serve as a suction tube as well as to convey a rinsing liquid into the cavity as it is being formed.

Synchronous rotation and operation of the controller 30 to enlarge the dimensions of the loop structure 20 during the procedure allows the physician to achieve a create a cavity C of desired dimension. Representative dimensions for a cavity C will be discussed in greater detail later.

B. Deployment and Use of the Brush Tool in a Vertebral Body

When, for example, the brush tool 38 is used, the physician preferable withdraws the bristles 46 during their passage through the guide sheath 34, in the manner shown in FIG. 6.

Figure 26:
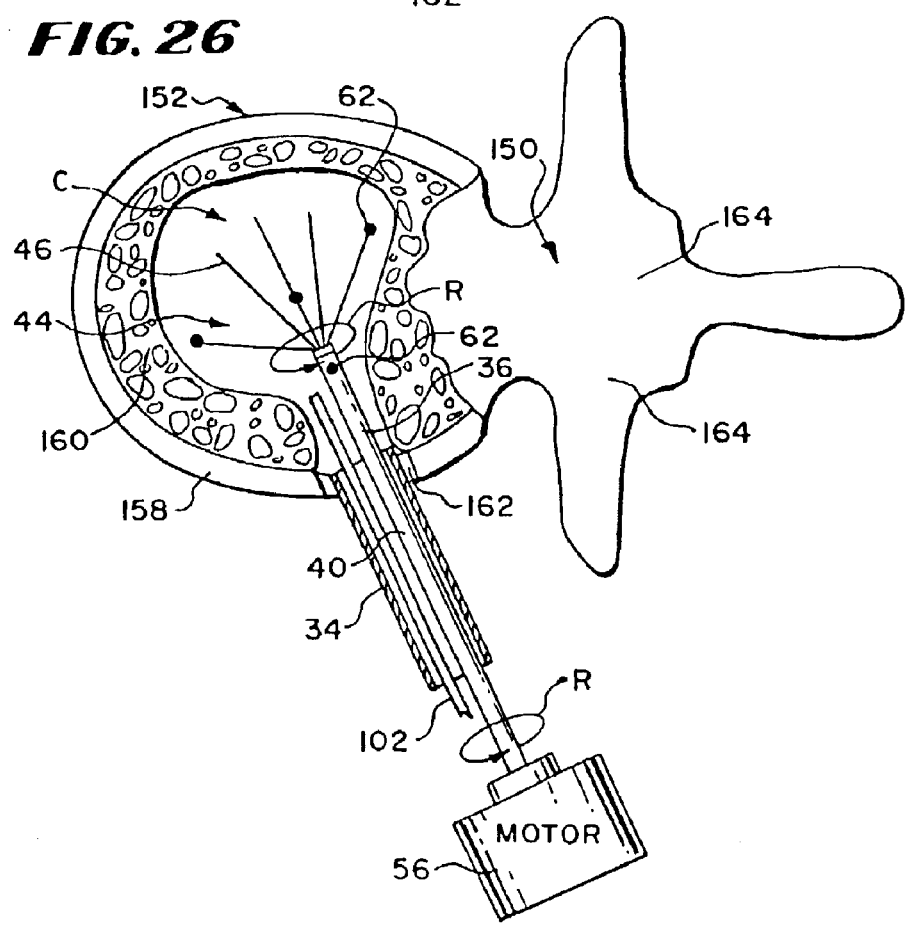
FIG. 26 is a top view of the vertebra shown in FIG. 23, with the tool shown in FIG. 5 deployed to cut cancellous bone by rotating the brush structure, thereby forming a cavity.

Referring to FIG. 26, when the brush tool 38 is deployed in cancellous bone 160 free of the guide sheath 34, the physician advances the bristles 46 a desired distance (as shown in FIG. 5), aided by radiologic monitoring of the markers 62, or the indicia 32 previously described, or both. The physician connects the drive shaft 40 to the motor 56 to rotate the bristles 46, creating the brush structure 44. As FIG. 26 shows, the rotating brush structure 44 cuts cancellous bone 160 and forms a cavity C. The suction tube 102 (or a lumen 128 in the drive shaft 40, as shown in FIG. 16) introduces a rinsing fluid (with an anticoagulant, if desired) and removes cancellous bone cut by the brush structure 44. By periodically stopping rotation of the brush structure 44 and operating the controller 60 (previously described) to increase the forward extension of the bristles 46, the physician able over time to create a cavity C having the desired dimensions.

C. Deployment and use of the Linear Tools in a Vertebral Body

When, for example, one of the linear movement tools 66 or 90 are used, the physician preferable withdraws the blade 78 or the transmitter 92 into the catheter tube 68 in the manner shown in FIG. 20, until the distal end 76 of the catheter tube 68 is free of the guide sheath 34.

Figure 27:
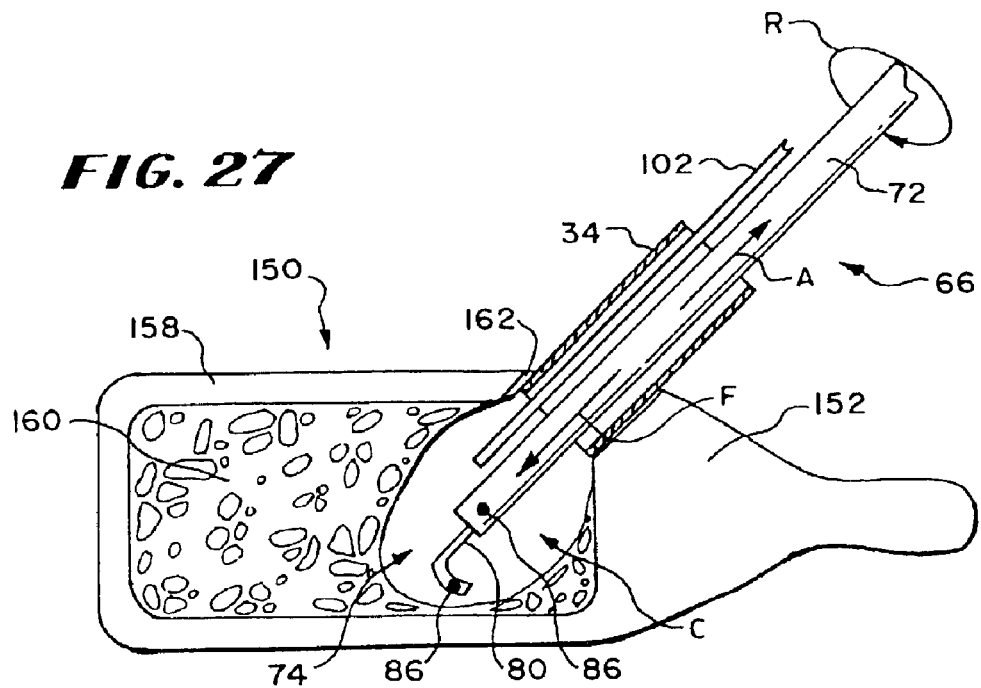
FIG. 27 is a side view of the vertebra shown in FIG. 23, with the tool shown in FIG. 17 deployed to cut cancellous bone by moving the blade structure in a linear path, thereby forming a cavity.

Referring to FIG. 27, using the blade tool 66, the physician operates the stylet 80 forward (arrow F) and aft (arrow A) to move the blade 78 in a linear path through cancellous bone 160. The blade 78 scrapes loose and cuts cancellous bone 160 along its path, which the suction tube 102 removes. A cavity C is thereby formed. Synchronous rotation (arrow R) and linear movement (arrows F and A) of the blade 78 allow the physician to create a cavity C having a desired dimension.

Figure 28:
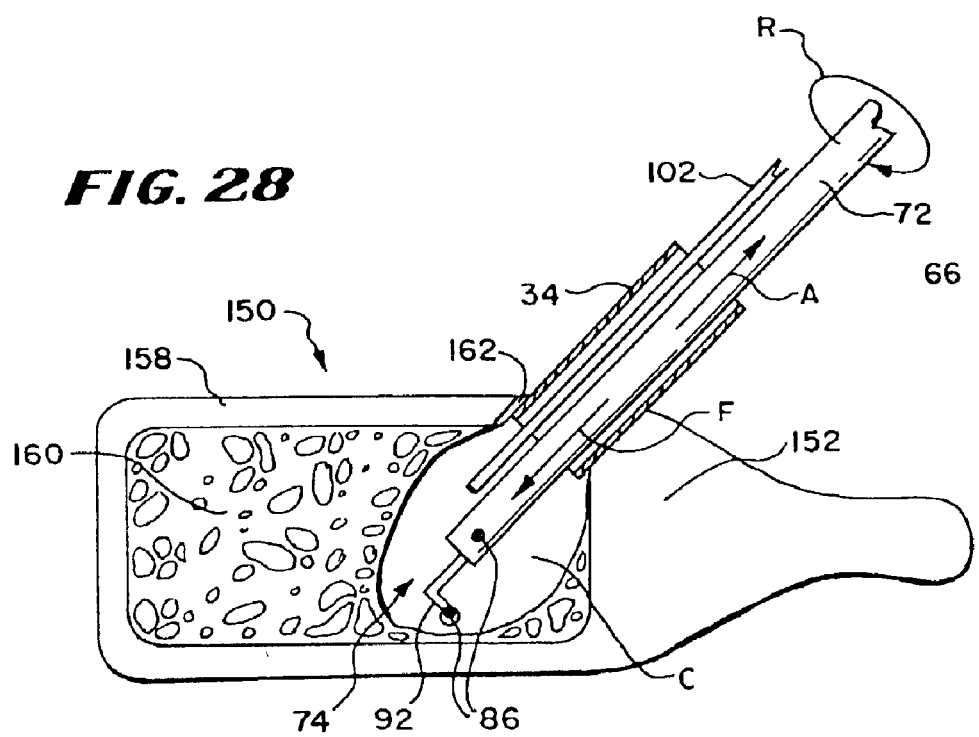
FIG. 28 is a side view of the vertebra shown in FIG. 23, with the tool shown in FIG. 22 deployed to cut cancellous bone using an energy transmitter, which is both rotatable and movable in a linear path, thereby forming a cavity.

Referring to FIG. 28, using the energy transmitting tool 90, the physician rotates (arrow R) and pushes or pulls upon the stylet 80 (arrows F and A) to position the energy transmitter 92 at desired locations in cancellous bone 160. The markers 86 aid the location process. Transmission by the transmitter 92 of the selected energy cuts cancellous bone 160 for removal by the suction tube 102. A cavity C is thereby formed. Through purposeful maneuvering of the transmitter 92, the physician achieves a cavity C having the desired dimension.

D. Deployment of Other Tools into the Cavity

Figure 29:
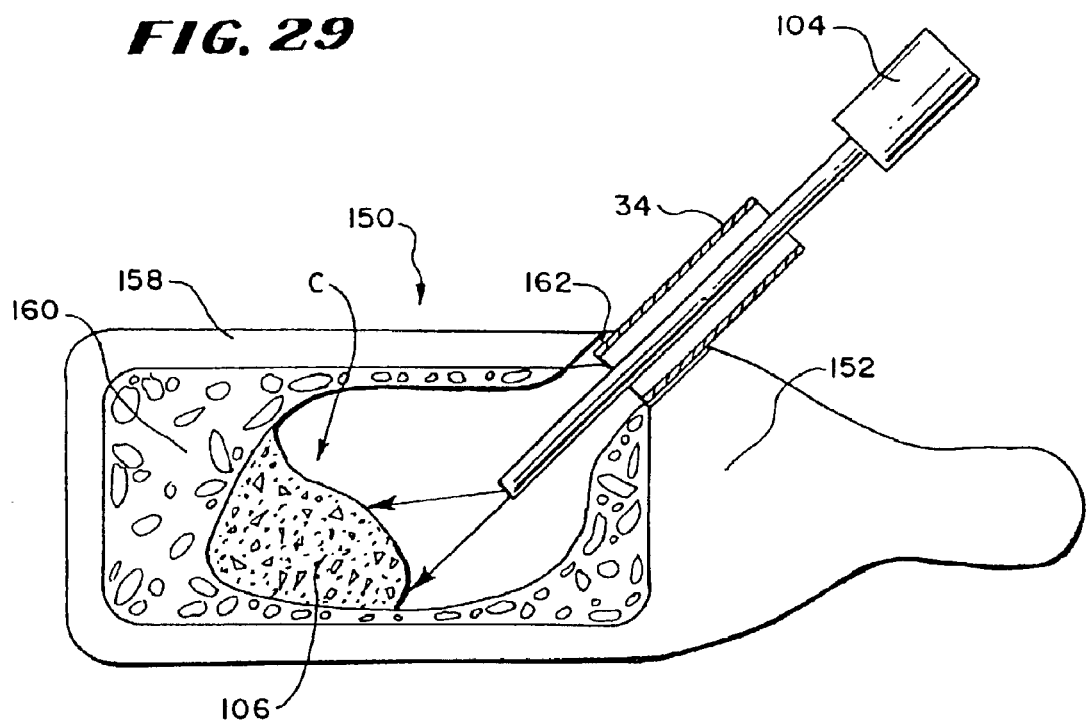
FIG. 29 is a side view of the vertebra shown in FIG. 23, after formation of a cavity by use of one of the tools shown in FIGS. 25 to 28, and with a second tool deployed to introduce material into the cavity for therapeutic purposes.

Once the desired cavity C is formed, the selected tool 10, 38, 66, 90, 106, or 138 is withdrawn through the guide sheath 34. As FIG. 29 shows, an other tool 104 can now be deployed through the guide sheath 34 into the formed cavity C. The second tool 104 can, for example, perform a diagnostic procedure. Alternatively, the second tool 104 can perform a therapeutic procedure, e.g., by dispensing a material 106 into the cavity C, such as, e.g., bone cement, allograft material, synthetic bone substitute, a medication, or a flowable material that sets to a hardened condition. Further details of the injection of such materials 106 into the cavity C for therapeutic purposes are found in U.S. Pat. Nos. 4,969,888 and 5,108,404 and in copending U.S. patent application Ser. No. 08/485,394, which are incorporated herein by reference.

E. Bone Cavity Dimensions

The size of the cavity C varies according to the therapeutic or diagnostic procedure performed.

At least about 30% of the cancellous bone volume needs to be removed in cases where the bone disease causing fracture (or the risk of fracture) is the loss of cancellous bone mass (as in osteoporosis). The preferred range is about 30% to 90% of the cancellous bone volume. Removal of less of the cancellous bone volume can leave too much of the diseased cancellous bone at the treated site. The diseased cancellous bone remains weak and can later collapse, causing fracture, despite treatment.

However, there are times when a lesser amount of cancellous bone removal is indicated. For example, when the bone disease being treated is localized, such as in avascular necrosis, or where local loss of blood supply is killing bone in a limited area, the selected tool 10, 38, 66, 90, 106, or 138 can remove a smaller volume of total bone. This is because the diseased area requiring treatment is smaller.

Another exception lies in the use of a selected tool 10, 36, 66, 90, 106, or 138 to improve insertion of solid materials in defined shapes, like hydroxyapatite and components in total joint replacement. In these cases, the amount of tissue that needs to be removed is defined by the size of the material being inserted.

Yet another exception lays the use of a selected tool 10, 36, 66, 90, 106, or 138 in bones to create cavities to aid in the delivery of therapeutic substances, as disclosed in copending U.S. patent application Ser. No. 08/485,394. In this case, the cancellous bone may or may not be diseased or adversely affected. Healthy cancellous bone can be sacrificed by significant compaction to improve the delivery of a drug or growth factor which has an important therapeutic purpose. In this application, the size of the cavity is chosen by the desired amount of therapeutic substance sought to be delivered. In this case, the bone with the drug inside is supported while the drug works, and the bone heals through exterior casting or current interior or exterior fixation devices.

IV. Single Use Sterile Kit

A single use of any one of the tools 10, 38, 138, 106, 66, or 90 creates contact with surrounding cortical and cancellous bone. This contact can damage the tools, creating localized regions of weakness, which may escape detection. The existence of localized regions of weakness can unpredictably cause overall structural failure during a subsequent use.

In addition, exposure to blood and tissue during a single use can entrap biological components on or within the tools. Despite cleaning and subsequent sterilization, the presence of entrapped biological components can lead to unacceptable pyrogenic reactions.

As a result, following first use, the tools may not meet established performance and sterilization specifications. The effects of material stress and damage caused during a single use, coupled with the possibility of pyrogen reactions even after resterilization, reasonably justify imposing a single use restriction upon the tools for deployment in bone.

To protect patients from the potential adverse consequences occasioned by multiple use, which include disease transmission, or material stress and instability, or decreased or unpredictable performance, each single use tool 10, 38, 66, 90, 106, or 138 is packaged in a sterile kit 500 (see FIGS. 30 and 31) prior to deployment in bone.

Figure 30:
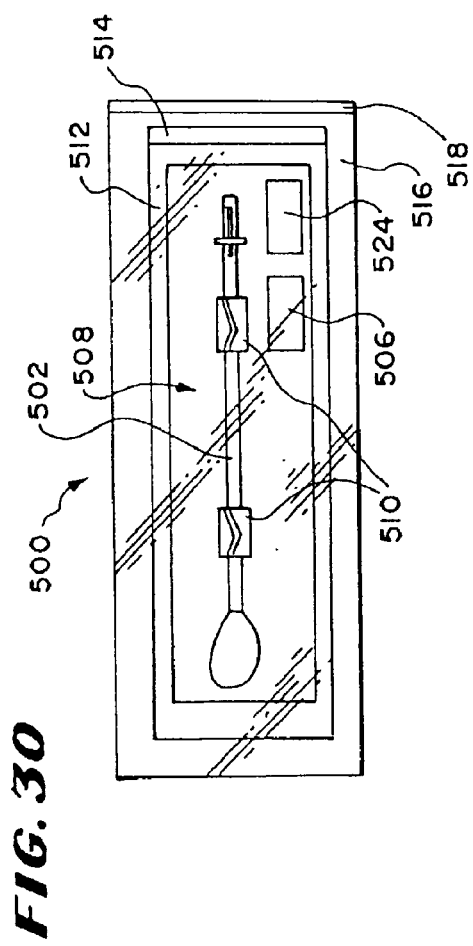
FIG. 30 is a plan view of a sterile kit to store a single use cavity forming tool of a type previously shown.
Figure 31:
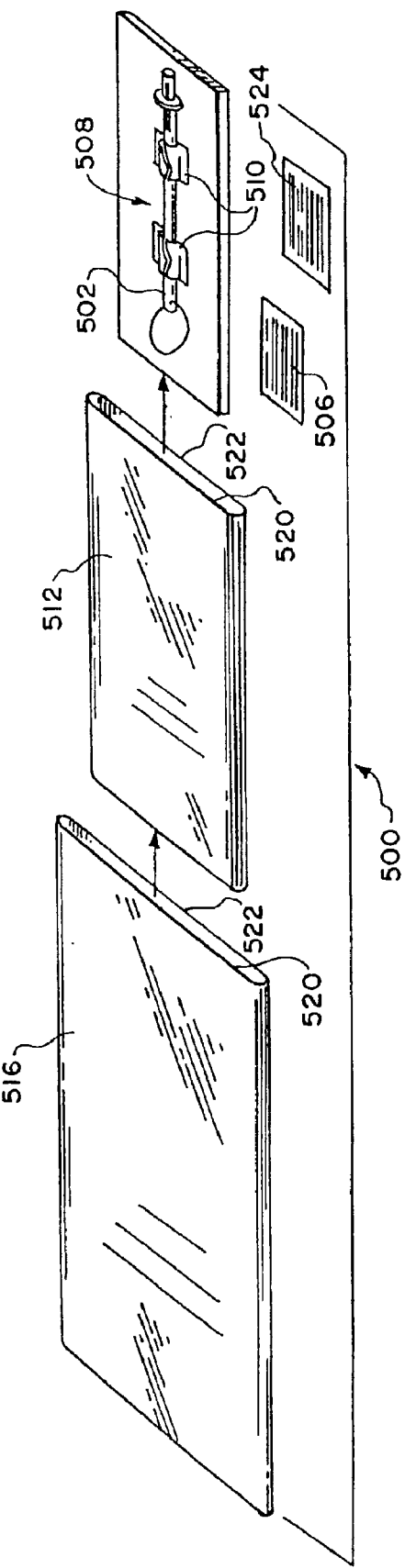
FIG. 31 is an exploded perspective view of the sterile kit shown in FIG. 30.

As FIGS. 30 and 31 show, the kit 500 includes an interior tray 508. The tray 508 holds the particular cavity forming tool (generically designated 502) in a lay-flat, straightened condition during sterilization and storage prior to its first use. The tray 508 can be formed from die cut cardboard or thermoformed plastic material. The tray 508 includes one or more spaced apart tabs 510, which hold the tool 502 in the desired lay-flat, straightened condition.

The kit 500 includes an inner wrap 512, which is peripherally sealed by heat or the like, to enclose the tray 508 from contact with the outside environment. One end of the inner wrap 512 includes a conventional peal-away seal 514 (see FIG. 31), to provide quick access to the tray 508 upon instance of use, which preferably occurs in a sterile environment, such as within an operating room.

The kit 500 also includes an outer wrap 516, which is also peripherally sealed by heat or the like, to enclosed the inner wrap 512. One end of the outer wrap 516 includes a conventional peal-away seal 518 (see FIG. 31), to provide access to the inner wrap 512, which can be removed from the outer wrap 516 in anticipation of imminent use of the tool 502, without compromising sterility of the tool 502 itself.

Both inner and outer wraps 512 and 516 (see FIG. 31) each includes a peripherally sealed top sheet 520 and bottom sheet 522. In the illustrated embodiment, the top sheet 520 is made of transparent plastic film, like polyethylene or MYLAR™ material, to allow visual identification of the contents of the kit 500. The bottom sheet 522 is made from a material that is permeable to EtO sterilization gas, e.g., TYVEC™ plastic material (available from DuPont).

The sterile kit 500 also carries a label or insert 506, which includes the statement "For Single Patient Use Only" (or comparable language) to affirmatively caution against reuse of the contents of the kit 500. The label 506 also preferably affirmatively instructs against resterilization of the tool 502. The label 506 also preferably instructs the physician or user to dispose of the tool 502 and the entire contents of the kit 500 upon use in accordance with applicable biological waste procedures. The presence of the tool 502 packaged in the kit 500 verifies to the physician or user that the tool 502 is sterile and has not be subjected to prior use. The physician or user is thereby assured that the tool 502 meets established performance and sterility specifications, and will have the desired configuration when expanded for use.

The kit 500 also preferably includes directions for use 524, which instruct the physician regarding the use of the tool 502 for creating a cavity in cancellous bone in the manners previously described. For example, the directions 524 instruct the physician to deploy and manipulate the tool 502 inside bone to cut cancellous bone and form a cavity. The directions 524 can also instruct the physician to fill the cavity with a material, e.g., bone cement, allograft material, synthetic bone substitute, a medication, or a flowable material that sets to a hardened condition.

The features of the invention are set forth in the following claims.

We claim:

1. A method for creating a cavity in cancellous bone comprising providing a cannula having an axis that establishes a percutaneous path leading into bone, providing a shaft having an axis and a distal end portion adapted to be deployed inside the bone through the cannula, said distal end portion having a cavity forming structure comprising a surface which directly contacts cancellous bone in response to linear movement of the shaft along the axis of the cannula, deploying the cannula percutaneously to establish a path leading to inside bone, introducing the shaft by movement within and along the axis of the cannula to deploy the cavity forming structure inside the cancellous bone, moving the shaft linearly along, and not rotatingly about the axis of the cannula to cause the surface to form a cavity in the cancellous bone.

2. A method according to claim 1, further including the step of filling the cavity with a filing material.

3. A method according to claim 1 wherein the cavity forming structure is adapted to be deployed at an axis that transverses the axis of the shaft.

4. A method according to claim 1, further including extending the cavity forming structure, in situ radially from the shaft.

5. A method according to claim 1 wherein the surface carries at least one marker to aid visualizing the cavity forming structure inside bone, further including observing the marker to visualize the cavity forming structure inside bone.

6. A method for treating bone comprising providing a cannula having a distal end and an axis that establishes a percutaneous path leading into the bone, providing a shaft having an axis and adapted to be deployed inside bone through the cannula including a cavity forming structure carried by the shaft adapted to extend beyond the distal end of the cannula and comprising a surface which directly contacts cancellous bone in response to linear movement of the shaft along the axis of the cannula, deploying the cannula percutaneously to establish a path leading to inside bone, introducing the shaft by movement within and along the axis of the cannula to deploy the cavity forming structure inside bone, and moving the shaft linearly along, and not rotatingly about the axis of the cannula to cause the surface to contact cancellous bone to form a cavity.

7. A method according to claim 6, further including filling the cavity with a material.

8. A method according to claim 6 wherein the cavity forming structure is adapted to be deployed at an axis that transverses the axis of the shaft.

9. A method according to claim 6, further including extending the cavity forming structure, in situ radially from the shaft.

10. A method according to claim 6 wherein the surface carries at least one marker to aid visualizing the cavity forming structure inside bone, further including observing the marker to visualize the cavity forming structure inside bone.

11. A method for, treating a vertebral body by creating a cavity, wholly within the vertebral body in cancellous bone comprising providing a cannula having an axis that establishes a percutaneous path leading into bone, providing a shaft having an axis and a distal end portion adapted to be deployed inside the bone through the cannula, said distal end portion having a cavity forming structure adapted to be extended in situ radially from the shaft and comprising a surface which directly contacts cancellous bone in response to linear movement of the shaft along the axis of the cannula, deploying the cannula percutaneously to establish a path leading to inside bone, introducing the shaft by movement within and along the axis of the cannula to deploy the cavity forming structure inside the cancellous bone, extending the cavity forming structure in situ radially from the shaft, and moving the shaft linearly along the axis of the cannula to cause the surface to form a cavity, wholly within the vertebral body in the cancellous bone.

12. A method according to claim 11, further including filling the cavity with a filling material.

13. A method according to claim 11 wherein the cavity forming structure is adapted to be deployed at an axis that transverses the axis of the shaft.

14. A method according to claim 11 wherein the surface carries at least one marker to aid visualizing the cavity forming structure inside bone, further including observing the marker to visualize the cavity forming structure inside bone.

15. A method for treating a vertebral body by creating a cavity wholly within the vertebral body comprising providing a cannula having a distal end and an axis that establishes a percutaneous path leading into the bone, providing a shaft having an axis and adapted to be deployed inside bone through the cannula including a cavity forming structure carried by the shaft adapted to extend beyond the distal end of the cannula and be extended in situ radially from the shaft and comprising a surface which directly contacts cancellous bone in response to linear movement of the shaft along the axis of the cannula, deploying the cannula percutaneously to establish a path leading to inside bone, introducing the shaft by movement within and along the axis of the cannula to deploy the cavity forming structure inside cancellous bone, extending the cavity forming structure in situ radially from the shaft, and moving the shaft linearly along the axis of the cannula to cause the surface to contact cancellous bone to from a cavity wholly within the vertebral body in the cancellous bone.

16. A method according to claim 15, further including filling the cavity with a material.

17. A method according to claim 15 wherein the cavity forming structure is adapted to be deployed at an axis that transverses the axis of the shaft.

18. A method according to claim 15 wherein the surface carries at least one marker to aid visualizing the cavity forming structure inside bone, further including observing the marker to visualize the cavity forming structure inside bone.

19. A method for treating a vertebral body by creating a cavity wholly inside the vertebral body in cancellous bone comprising providing a cannula having an axis that establishes a percutaneous path leading into bone, providing a shaft having an axis and a distal end portion adapted to be deployed inside the bone through the cannula, said distal end portion having a cavity forming structure adapted to be extended in situ radially from the shaft and comprising a surface which directly contacts the cancellous bone in response to movement of the shaft, deploying the cannula percutaneously to establish a path leading to inside bone, introducing the shaft by movement within and along the axis of the cannula to deploy the cavity forming structure inside the cancellous bone, extending the cavity forming structure in situ radially from the shaft, and moving the shaft to cause the surface to form a cavity wholly within the vertebral body in the cancellous bone.

20. A method according to claim 19, further including filling the cavity with a filling material.

21. A method according to claim 19 wherein the cavity forming structure is adapted to be deployed at an axis that transverses the axis of the shaft.

22. A method according to claim 19 wherein the surface carries at least one marker to aid visualizing the cavity forming structure inside bone, further including observing the marker to visualize the cavity forming structure inside bone.

23. A method for treating a vertebral body by creating a cavity wholly within the vertebral body in cancellous bone comprising providing a cannula having a distal end an axis that establishes a percutaneous path leading into bone, providing a shaft having an axis and adapted to be deployed inside bone through the cannula including a cavity forming structure carried by the shaft adapted to extend beyond the distal end of the cannula and, be extended in situ radially from the shaft and comprising a surface which directly contacts the cancellous bone in response to movement of the shaft, deploying the cannula percutaneously to establish a path leading to inside bone, introducing the shaft by movement within and along the axis of the cannula to deploy the cavity forming structure inside the cancellous bone, extending the cavity forming structure in situ radially from the shaft, and moving the shaft to cause the surface to contact cancellous bone to form a cavity wholly within the vertebral body in the cancellous bone.

24. A method according to claim 23, further including filling the cavity with a material.

25. A method according to claim 23 wherein the cavity forming structure is adapted to be deployed at an axis that transverses the axis of the shaft.

26. A method according to claim 23 wherein the surface carries at least one marker to aid visualizing the cavity forming structure inside bone, further including observing the marker to visualize the cavity forming structure inside bone.

* * * * *

UNITED STATES PATENT AND TRADEMARK OFFICE
CERTIFICATE OF CORRECTION

PATENT NO. : 6,863,672 B2
DATED : March 8, 2005
INVENTOR(S) : Mark A. Reiley and Arie Scholten It is certified that error appears in the above-identified patent and that said Letters Patent is hereby corrected as shown below:

Column 13,
Lines 19 and 44, after "along" delete "," (comma).
Line 24, after "with a" delete "filing" and substitute -- filling --.
Lines 29 and 61, after "structure" delete "," (comma).

Column 14,
Line 3, after "for" delete "," (comma).
Lines 4 and 22, after "cavity" delete "," (comma).

Column 16,
Line 9, after "and" delete "," (comma).

Signed and Sealed this

Twenty-third Day of August, 2005

JON W. DUDAS
*Director of the United States Patent and Trademark Office*